United States Patent [19]

Ichiro

[11] Patent Number: 4,847,151
[45] Date of Patent: Jul. 11, 1989

[54] ELECTRIC CONDUCTOR COVERED BY COVERING MATERIAL

[75] Inventor: Shibanai Ichiro, Tokyo, Japan

[73] Assignee: Japan Liquid Crystal Co., Ltd., Tokyo, Japan

[21] Appl. No.: 116,371

[22] Filed: Nov. 2, 1987

Related U.S. Application Data

[63] Continuation-in-part of Ser. No. 41,662, Apr. 20, 1987, Pat. No. 4,722,815, which is a continuation of Ser. No. 809,081, Dec. 12, 1985, abandoned.

[51] Int. Cl.$^4$ .................. B32B 9/00; B32B 15/00; H01B 7/00
[52] U.S. Cl. .................... 428/389; 428/372; 428/379; 428/383; 428/907; 174/110 PM; 174/110 V; 174/120 SR
[58] Field of Search ............... 428/375, 379, 389, 907, 428/383, 372; 174/110 PM, 110 V, 120 SR

[56] References Cited

U.S. PATENT DOCUMENTS 3,252,834  5/1966  Vincent .................. 428/907 X
3,503,800  3/1970  Eddy .................... 428/907 X

FOREIGN PATENT DOCUMENTS 0237977  11/1959  Australia .
0233384   3/1960  Australia .
0707133   4/1954  United Kingdom .
0853612  11/1960  United Kingdom .
0893819   4/1962  United Kingdom .

*Primary Examiner*—Lorraine T. Kendell
*Attorney, Agent, or Firm*—Burgess, Ryan & Wayne

[57] ABSTRACT

The termite repellent and/or the rodent repellent is entrapped in cyclodextrin as a cyclodextrin inclusion compound.

The termite repellent may be: for example, a copper compound, such as copper naphthenate, or cuprous oxide; an organic phosphorus insecticide, such as chlorpyrifos, phoxim (i.e., phenylglyoxylonitriloxime O,O-diethyl phosphorothioate), fenitrothion, or prothiophos (CAS No. 34643-46-4); carbamate insecticide, such as carbaryl; pyrethroids insecticide, such as permethrin, or furamethrin.

·The rodent repellent may be: for example, cycloheximide, i.e., naramycin; or organic tin compound, such as dibutyltin oxide, or dibutyltin laurate.

The cyclodextrin inclusion compound of termite repellent and/or rodent repellent and glycitols are mixed with a covering material of the electric wire or cable.

The chief ingredient of the covering material is a synthetic resin or synthetic rubber. The synthetic resin may be polyvinyl chloride, or polyethylene. The synthetic rubber may be chloroprene rubber or ethylene propylene rubber.

The mixture is extruded onto an electric wire or cable bny extrusion coating to form a termite and/or rodent resistant coating.

11 Claims, 1 Drawing Sheet

ELECTRIC CONDUCTOR COVERED BY COVERING MATERIAL

CROSS REFERENCE TO RELATED APPLICATIONS

This application is a Continuation-in-Part Application of U.S. Ser. No. 041,662, filed on Apr. 20, 1987, and now U.S. Pat. No. 4,722,815, which is a Continuation Application of U.S. Ser. No. 809,081 filed on Dec. 12, 1985, and now abandoned.

TECHNICAL FIELD OF THE INVENTION

The present invention relates to an electric conductor covered by covering material. More specifically, the present invention relates to an electric wire or an electric cable, which has resistance to termite and/or rodent.

BACKGROUND OF THE INVENTION

Recently, an electric wire or cable, which has resistance to termite and/or rodent, is required.

In order to meet with such a requirement, a conventionally known electric wire or cable is covered by extrusion coating of a covering material, the chief ingredient of which material is a synthetic resin or a synthetic rubber and which material contains a termite repellent and/or a rodent repellent.

For example, in a typical method for manufacturing a conventionally known termite resistant cable, a master batch is previously prepared by mixing a termite repellent with synthetic resin or synthetic rubber. Termite repellent is, for example, copper naphthenate, organic phosphate, carbamate insecticide, or pyrethroids. The synthetic resin is, for example, polyvinyl chloride, or polyethylene. The synthetic rubber is, for example, chloroprene rubber.

The master batch thus prepared is mixed at a predetermined ratio with coating material. The thus obtained mixture is extruded onto a cable by extrusion coating to form a conventional termite resistant cable.

When a covering material, the chief ingredient of which is a synthetic resin or a synthetic rubber and which contains a termite repellent and/or a rodent repellent, is extruded onto a cable, the termite repellent and/or a rodent repellent is often vaporized or heat decomposed by the heat of a high temperature, i.e., between about 160° and 220° C., generated during extrusion coating. Accordingly, the percentage of retension of the repellent in the coating is low. The percentage of retension described above is defined as the percentage of the amount of the repellent retained in the product to that of the repellent added to the raw material.

Consequently, if a sufficiently high termite resistant effect or rodent resistant effect is necessary, a large amount of termite repellent and/or rodent repellent must be added.

As a result, the following problems are observed in the conventional termite and/or rodent resistant cable. Since the termite repellent and rodent repellent are expensive, the cost for manufacturing such a conventional termite and/or rodent resistant cable is high. Further, since the termite repellent and rodent repellent are easily heat decomposed, the heat resisting characteristic of the conventional termite and/or rodent resistant cable is low. Similarly, the mechanical characteristic of the termite and/or rodent resistant cable is low.

Furthermore, since the termite repellent and rodent repellent are easily heat vaporized, the working environment for manufacturing the conventional termite and/or rodent resistant cable is bad.

Under these circumstances, I have previously invented a process for producing a smelling synthetic resin product which comprises forming a cyclodextrin inclusion compound consisting of a perfume included in cyclodextrin, drying and powdering the obtained cyclodextrin inclusion compound and mixing the obtained powder with a synthetic resin compound (cf. Japanese Pat. No. 1090861).

I have further invented a process for producing an insectifugal and insecticidal film which comprises forming a cyclodextrin inclusion compound consisting an insectifugal and insecticidal agent included in cyclodextrin, drying and powdering the obtained cyclodextrin inclusion compound and mixing the obtained powder with a synthetic resin compound followed by molding into a film (cf. Japanese Patent Laidopen No. Sho 61-65805 and Japanese Patent Laid-open No. Sho 61-137803).

A smelling synthetic resin product produced by forming a cyclodextrin inclusion compound consisting of a perfume included in cyclodextrin, powdering and drying the obtained cyclodextrin inclusion compound and mixing the obtained powder with a synthetic resin compound is much more excellent than those produced by conventional methods. Subsequent studies have proved that not only perfumes but also various substances such as insectifuges, mildewproofing agents and rust preventives may be formed into a cyclodextrin inclusion compound so long as it can be included in cyclodextrin to thereby produce synthetic resin products having the effect of each substance.

However, these cyclodextrin inclusion compounds consisting of a perfume included in cyclodextrin cannot be used in practice in synthetic resin products of a high molding temperature, i.e., 180° C. or above. Cyclodextrin per se is stable at high temperatures and shows no chemical change so that it is theoretically possible to use it in a synthetic resin of a high molding temperature. However, pure cyclodextrin is so expensive that decomposed starches containing cyclodextrin are employed in practice. These decomposed starches contain reducing sugars which would be taken place chemical change and charred when molded at a high temperature.

Although there is no problem in the production of a synthetic resin product having various effects by forming a cyclodextrin inclusion compound consisting of perfume(s), insectifuge(s), or rust preventive(s) included in cyclodextrin, drying and powdering the obtained cyclodextrin inclusion compound and mixing the obtained powder with a synthetic resin compound on a laboratory scale with the use of pure cyclodextrin, there remains a problem to be solved in the production thereof on an industrial scale.

In addition, the volatility of each substance is somewhat depressed by including the same in cyclodextrin to thereby form a cyclodextrin inclusion compound, which allows its effect to persist for a much longer period than with conventional products. However, the persistence is somewhat insufficient yet.

OBJECT OF THE INVENTION

It is an object of the present invention to obviate the problems inherent in the conventional termite and/or rodent resistant electric wire and/or cable.

SUMMARY OF THE INVENTION

According to the present invention, the termite repellent and/or the rodent repellent is entrapped in cyclodextrin as a cyclodextrin clathrate compound. The "cyclodextrin clathrate compound" is also referred to as "cyclodextrin inclusion compound" or "cyclodextrin clathrate inclusion compound". The cyclodextrin clathrate compound is stable against heat.

The obtained cyclodextrin clathrate compound of termite repellent and/or rodent repellent and glycitol are mixed with a covering material, the chief ingredient of which is a synthetic resin or synthetic rubber. The mixture is extruded onto an electric wire or cable by extrusion coating to form a termite and/or rodent resistant coating.

BRIEF DESCRIPTION OF THE DRAWINGS

The present invention will now be explained in detail with reference to the attached drawings, wherein.

PREFERRED EMBODIMENTS

Figure 1:
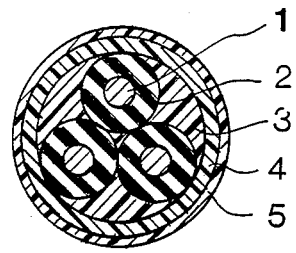
FIGS. 1 through 4 illustrate a cross sectional views of some preferred embodiments of the present invention.

As described above, according to the present invention, the termite repellent and/or the rodent repellent is entrapped in cyclodextrin as a cyclodextrin inclusion compound. The obtained cyclodextrin inclusion compound of termite repellent and/or rodent repellent and glycitol are mixed with a covering material, the chief ingredient of which is a synthetic resin or synthetic rubber. The mixture is extruded onto an electric wire or cable by extrusion coating to form a termite and/or rodent resistant coating.

Under these circumstances, termite repellent and/or rodent repellent are inactivated by formulating into the cyclodextrin inclusion compound and coated with the glycitol to thereby enhance the persistence of the effects thereof.

The cyclodextrin inclusion compound of the present invention exhibiting the above-mentioned effects may be produced by mixing way of a saturated aqueous solution method or a kneading method. That is, a termite repellent, rodent repellent, or a mixture of a termite repellent and rodent repellent at a predetermined ratio, is mixed with and agitated with either one of a reduced cyclodextrin millet jelly, mixture of the reduced cyclodextrin millet jelly and powder cyclodextrin, and a mixture of a reduced millet jelly and cyclodextrin.

In this case, if necessary, water may be added to the reduced cyclodextrin millet jelly or reduced millet jelly, but no water may be added since the reduced cyclodextrin millet jelly or the millet jelly contains some water.

Then, the obtained material containing the cyclodextrin inclusion compound and glycitol is dried and powdered.

The reduced millet jelly used in the present invention is obtained by hydrolyzing starch with an acid of an enzyme to give a maltoligosaccharide mixture comprising glucose, maltose, maltoriose and similar compounds and hydrogenating the mixture in the presence of a nickel catalyst under elevated pressure. Thus, reductive terminals of the reducing sugars are hydrogenated to give the corresponding glycitols. That is, glucose, maltose, maltoriose are converted into sorbitol, maltitol and maltotritol, respectively, and lose their reductivity. Thus, the D.E. (dextrose equivalent: the ratio of reducing sugars to the total solid matters) of the mixture turns to 0. Therefore, the mixture becomes more stable to heat and shows little coloration caused by a reaction with amino radicals contained in amino acids or the like, i.e., aminocarbonyl reaction.

The reduced cyclodextrin millet jelly used in the present invention includes the above-mentioned reduced millet jelly containing cyclodextrin. Since cyclodextrin exhibits nor reductivity, the D.E. of the same is 0. In practice, the reduced cyclodextrin millet jelly can be obtained by catalytically reducing a millet jelly cyclodextrin containing cyclodextrin, e.g., Celldex CH-20 or CH-30 mfg. by Nippon Shokuhin Kakao K.K., in the manner as described above. The cyclodextrin contained therein shows no change by the above procedure, but reducing sugars contained as impurities in the cyclodextrin containing decomposed starch other than the cyclodextrin are reduced and converted into the corresponding glycitols which glycitols are chemically stable.

The termite repellent used in the present invention may be: for example, copper compound, such as copper naphthenate, or cuprous oxide an organic phosphorus insecticide, such as chlorpyrifos, phoxim (i.e., phenylglyoxylonitriloxime 0,0-diethyl phosphorothioate), fenitrothion, or prothiophos (CAS No. 34643-46-4); carbamate insecticide, such as carbaryl; or pyrethroids insecticide, such as permethrin, or furamethrin.

The rodent repellent may be: for example, cycloheximide, i.e., naramycin; or organic tin compound, such as dibutyltin oxide, or dibutyltin laurate.

The cyclodextrin has a large cavity in its molecule, wherein the termite repellent and/or the rodent repellent is included, while the repellent is hydrogen bonded with the cyclodextrin, so that a cyclodextrin inclusion compound, which is stable against heat, is formed.

When the cable or wire is needed to be termite resistant and rodent resistant, as described above, after the termite repellent and the rodent repellent are mixed with each other, the mixture may be included in a cyclodextrin. In another method, after the termite repellent and the rodent repellent are independently included in cyclodextrins, the thus obtained cyclodextrin inclusion compound of termite repellent and the cyclodextrin inclusion compound of rodent repellent may be mixed with each other.

The content of the termite repellent and/or the rodent repellent contained in the cyclodextrin inclusion compound is usually between about 10 and 50 % by weight, though the content depends on the kinds of the termite repellent and the rodent repellent. When both the termite repellent and the roden repellent are used, the ratio of the repellents is determined taking the usage of the produced electric wire or cable into consideration.

Thereafter, the thus produced powder containing cyclodextrin inclusion compound of termite repellent and/or rodent repellent and glycitol are mixed with a covering material, which will be a coating or a surrounding of the electric wire or cable. More specifically, a cyclodextrin inclusion compound of termite repellent, a cyclodextrin inclusion compound of rodent repellent, or a mixture of the cyclodextrin inclusion compounds is added to the covering material, or a cyclodextrin inclusion compound of termite repellent and rodent repellent is added to the covering material.

The covering material of the present invention may be a composition, the chief ingradient of which is: a synthetic resin, such as a polyvinyl chloride resin, or an olefin resin, e.g., a polyethylene resin; or a synthetic rubber, such as a chloroprene rubber or an ethylene propylene rubber. The contents of the composition are selected taking the usage of the electric wire or cable into consideration.

According to the present invention, since the obtained powder to be mixed with the covering material contains not only cyclodextrin inclusion compound but also glycitol, the powder shows an excellent thermal stability, an excellent dispersibility and an excellent compatibility by effect of the glycitol.

Since the termite repellent and/or the rodent repellent in the cyclodextrin inclusion compound is not easily heat decomposed or vaporized, the amount of the cyclodextrin inclusion compound mixed to the covering material can be remarkably decreased compared with that of the termite repellent and/or the rodent repellent needed in a conventional electric wire or cable. The density of the termite repellent and/or the rodent repellent can be usually between about 0.1 and 5% by weight according to the present invention.

The percentage of the amount of the obtained powder containing cyclodextrin inclusion compound and glycitol to the total weight of the covering material is suitable to be between about 5 and 10 % by weight.

The covering material having the cyclodextrin inclusion compound of termite repellent and/or rodent repellent added therein is mixed in a conventionally well known mixing means.

The covering material may be extruded by means of a conventionally known extruder which is provided with a crosshead die.

As illustrated in FIG. 1, the covering material may be a termite resistant and/or rodent resistant covering 5 extruded by extrusion coating onto a sheath 4 of an electric cable which sheath surrounds conductors 1, insulations 2 and fillers 3.

Figure 2:
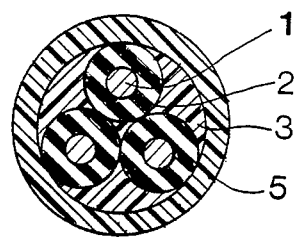

As illustrated in FIG. 2, the cyclodextrin inclusion compound may be added to the covering material, which forms a sheath 5 of an electric wire or cable, wherein a plurality of conductors 1 covered by insulations 2 are twisted and are surrounded by filler 3.

Figure 3:
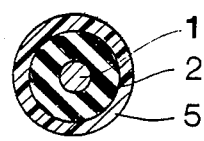

As illustrated in FIG. 3, the covering material may also be extruded by extrusion coating onto an insulation 2 which surrounds a conductor 1 as a termite resistant and/or rodent resistant covering 5. Thus, an electric wire or cable having a termite resistant and/or rodent resistant covering 5 is formed.

Figure 4:
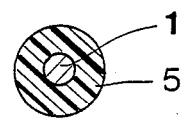

The covering material containing cyclodextrin inclusion compound may also be extruded by extrusion coating onto a conductor 1 as a termite resistant and/or rodent resistant insulating covering 5 as illustrated in FIG. 4.

In some cases, an air permeable protective cover, which is made of, for example, a coarse woven fabric or knitted fabric, may be disposed on the outer surface of the covering material of the present invention.

Since the termite repellent and/or the rodent repellent is protected by the cyclodextrin, it is not easily heat decomposed or vaporized. However, it is preferred that the mixing operation and the extrusion coating operation of the covering material is performed at a temperature as low as possible so as to minimize heat decomposition or vaporization of the termite repellent and/or the rodent repellent. For this purpose, it is preferred to increase amount of liquid additive, such as plasticizer, taking into consideration the mechanical characteristics and the electrical characteristics of the termite resistant and/or rodent resistant covering, so that the flowability of the covering material at a low temperature is improved.

The thickness of the termite resistant and/or rodent resistant covering is not specifically limited, however, the thickness is usually between about 0.1 and 3 mm.

According to the termite resistant and/or rodent resistant electric wire or cable of the present invention, the termite repellent and/or rodent repellent contained in the termite resistant and/or rodent resistant covering is stable against heat, since it is a cyclodextrin inclusion compound, and the cyclodextrin inclusion compound is coated with glycitol. Accordingly, only very little amount of the termite repellent and/or a rodent repellent is vaporized or heat decomposed during extrusion coating. Accordingly, the percentage of retension of the repellent in the coating is high.

Consequently, the amount of termite repellent and/or rodent repellent, which should be added to the covering material, can be small. As a result, the termite and/or rodent resistant wire or cable can be manufactured at a low cost. Furthermore, since the termite repellent and rodent repellent are not easily heat vaporized, the working environment for manufacturing the termite and/or rodent resistant cable is not deteriorated and is good. Further, the glycitols exert an effect of significantly prolonging the duration periods of the effects of the repellent.

EXAMPLES

Some specific examples of the present invention will now be described to show the unexpected advantages of the present invention.

Example 1

In order to obtain a cyclodextrin inclusion compound, 20 parts by weight of phoxim (i.e., phenylglyoxylonitriloxime 0,0-diethyl phosphorothioate) which is a termite repellent of an organic phosphorus insecticide were mixed with 30 parts by weight of powder beta-cyclodextrin and 50 parts by weight of a reduced millet jelly, and the mixture were agitated at a temperature of between 70° and 60° C. for between about 30 and 60 minutes. After a duration of between about 10 and 24 hours, wherein the mixture was left stand, the obtained cyclodextrin inclusion compound is dried and powdered by means of a drum type dryer or a spray type dryer.

Thereafter, the obtained powder containing cyclodextrin inclusion compound and glycitols was blended with a covering material, the chief gradient of which is polyvinyl chloride, in accordance with the following formulation.

polyvinyl chloride: 100 parts by weight
dioctyl phthalate: 50 parts by weight
calcium carbonate: 20 parts by weight
organic tin stabilizer: 5 parts by weight
obtained powder containing cyclodextrin inclusion compound and glycitols: 5 parts by weight After the above-listed materials were mixed with each other by means of a Henschel mixer and were kneaded by means of a Banbury mixer, they were extruded onto a sheath of an electric cable at a thickness of 1.0mm by means of an extruder provided with a crosshead die at an extrusion temperature of 160° C. Thus, an electric cable as illustrated in FIG. 1 was obtained.

Example 2

Using cycloheximide, i.e., a rodent repellent of an organic tin compound, a rodent resistant electric cable was manufactured in accordance with a method similar to that described with reference to Example 1 above.

Example 3

The mixture of Sumithion, i.e., an organic phosphorus insecticide manufactured by Sumitomo Chemical Co., Ltd., and phoxim, i.e., an organic phosphorus insecticide, was included in a cyclodextrin by using a reduced cyclodextrin millet jelly in place of powder cyclodextrin and a reduced millet jelly in accordance with a method similar to that explained with reference to Example 1 to form a cyclodextrin inclusion compound.

The obtained powder cyclodextrin containing inclusion compound and glycitols was blended with a covering material, the chief gradient of which is polyvinyl chloride, in accordance with the following formulation.

polyvinyl chloride; 100 parts by weight
dioctyl phthalate; 50 parts by weight
calcium carbonate; 20 parts by weight
organic tin stabilizer; 5 parts by weight
powder containing cyclodextrin inclusion compound and glycitols; 2 parts by weight After the above-listed materials were mixed with each other by means of a Henschel mixer and were kneaded by means of a Banbury mixer, they were extruded as a sheath of an electric cable as illustrated in FIG. 2 by means of an extruder provided with a crosshead die at an extrusion temperature of 160° C.

Example 4

In order to obtain a cyclodextrin inclusion compound, 20 parts by weight of permethrin which is a termite repellent were mixed with 10 parts by weight of powder beta-cyclodextrin and 70 parts by weight of a reduced cyclodextrin millet jelly, and the mixture were agitated at a temperature of between 70° and 60° C. for between about 30 and 60 minutes. After a duration of between about 10 and 24 hours, wherein the mixture was left stand, the obtained cyclodextrin inclusion compound is dried and powdered by means of a drum type dryer or a spray type dryer.

Thereafter, the obtained powder containing cyclodextrin inclusion compound and glycitols was blended with a covering material, the chief gradient of which is polyvinyl chloride, in accordance with the following formulation.

polyvinyl chloride: 100 parts by weight
dioctyl phthalate: 50 parts by weight
calcium carbonate; 20 parts by weight
organic tin stabilizer; 5 parts by weight
obtained powder containing cyclodextrin inclusion compound and glycitols; 3 parts by weight After the above-listed materials were mixed with each other by means of a Henschel mixer and were kneaded by means of a Banbury mixer, they were extruded onto an insulation of an electric cable by means of an extruder provided with a crosshead die at an extrusion temperature of 160° C. Thus, an electric cable as illustrated in FIG. 3 was obtained.

ADVANTAGES OF THE INVENTION

As described above, according to the present invention, the termite repellent and/or the rodent repellent is entrapped in cyclodextrin as a cyclodextrin inclusion compound by using reduced cyclodextrin millet jelly or a mixture of reduced millet jelly and cyclodextrin. Since reducing sugars contained as impurities in the decomposed starch are converted into glycitols in the reduced cyclodextrin millet jelly or the reduced millet jelly, the powder containing cyclodextrin inclusion compound and glycitols has an excellent thermal stability.

The cyclodextrin inclusion compound per se is not easily heat decomposed or vaporized. In addition to this, according to the present invention, since the cyclodextrin inclusion compound is coated by glycitols, its thermal stability is further enhanced. The percentage of retension of the termite repellent and/or the rodent repellent in the covering material of the electric wire or cable can be high. Accordingly, a considerably high termite resistant effect and/or rodent resistant effect can be achieved with small amount of the termite repellent and/or the rodent repellent. Since the amount of termite repellent and/or the rodent repellent can be small, the cost for manufacturing the termite and/or rodent resistant cable of the present invention is inexpensive. Further, no gas of the termite repellent and/or rodent repellent is generated during the extrusion, the working environment is not deteriorated. When cyclodextrin inclusion compounds of termite repellent and rodent repellent are separately prepared and are added to the covering material, the termite repellent and the rodent repellent can be used though they are incompatible with each other, since the repellents are not directly mixed with each other.

Further the glycitols exert an effect of significantly prolonging the duration periods of the effects of the termite repellent and/or the rodent repellent. Further, the glycitols enhance a compatibility of the powder, which contains cyclodextrin and glycitols, with synthetic resin or synthetic rubber and uniformly disperse the cyclodextrin. Accordingly, the covering material exert a uniform resistance to termite resistance and/or rodent.

What is claimed is:

1. An electric conductor covered by covering material, wherein said covering material comprises a synthetic resin or rubber, glycitol and a cyclodextrin inclusion compound, said compound being coated with said glycitol, and wherein said cyclodextrin inclusion compound being at least one of termite repellent and rodent repellent included in cyclodextrin, and wherein said inclusion compound is formed by mixing said repellent with at least one of:
   (a) a reduced cycoldextrin millet jelly,
   (b) a mixture of reduced cyclodextrin millet jelly and powdered cyclodextrin, and
   (c) a mixture of reduced millet jelly and cyclodextrin.

2. An electric conductor covered by covering material according to claim 1, wherein said covering material contains cyclodextrin inclusion compound of termite repellent.

3. An electric conductor covered by covering material according to claim 1, wherein said covering material contains cyclodextrin inclusion compound of rodent repellent.

4. An electric conductor covered by covering material according to claim 1, wherein said covering material contains cyclodextrin inclusion compound of termite repellent and rodent repellent.

5. An electric conductor covered by covering material according to claim 1, wherein said covering material contains cyclodextrin inclusion compound of termite repellent and cyclodextrin inclusion compound of rodent repellent.

6. An electric conductor covered by covering material according to claim 1, wherein chief ingredient of said covering material is a synthetic resin.

7. An electric conductor covered by covering material according to claim 6, wherein said synthetic resin is an olefin resin.

8. An electric conductor covered by covering material according to claim 6, wherein said synthetic resin is a vinyl chloride resin.

9. An electric conductor covered by covering material according to claim 1, wherein chief ingredient of said covering material is a synthetic rubber.

10. An electric conductor covered by covering material according to claim 1, wherein said termite repellent is selected form a group consisting of copper compound, organic phosphorus insecticide, carbamate insecticide, and pyrethroids insecticide.

11. An electric conductor covered by covering material according to claim 1, wherein said termite repellent is selected form a group consisting of cycloheximide and organic tin compound.

* * * * *